United States Patent [19]

Marschner et al.

[11] Patent Number: 5,405,993
[45] Date of Patent: Apr. 11, 1995

[54] REACTIVE FORMAZAN DYES AND HYDRAZONES

[75] Inventors: Claus Marschner, Speyer; Manfred Patsch, Wachenheim, both of Germany

[73] Assignee: BASF Aktiengesellschaft, Ludwigshafen, Germany

[21] Appl. No.: 288,242

[22] Filed: Aug. 9, 1994

Related U.S. Application Data

[62] Division of Ser. No. 117,686, Sep. 8, 1993.

[30] Foreign Application Priority Data

Sep. 9, 1992 [DE] Germany .................. 42 30 095.9

[51] Int. Cl.⁶ .................. C07C 251/86; C07C 309/29; C07C 309/35
[52] U.S. Cl. ...................... 560/308; 558/33; 562/57; 562/67; 562/427; 562/430
[58] Field of Search ............ 558/33; 560/308; 562/57, 67, 427, 430; 564/251

[56] References Cited

U.S. PATENT DOCUMENTS 2,748,021  5/1956  Van Allan ................. 562/57
4,757,135  7/1988  Schwaiger ............... 534/618

*Primary Examiner*—Mary C. Lee
*Assistant Examiner*—Fiona T. Powers
*Attorney, Agent, or Firm*—Oblon, Spivak, McClelland, Maier & Neustadt

[57] ABSTRACT

There are described formazan dyes of the formula

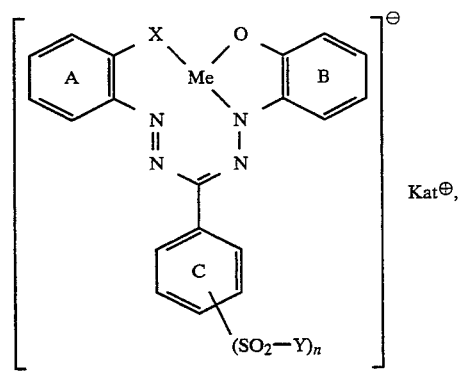

where
n is 1 or 2,
Kat● is the equivalent of a cation,
Me is copper or nickel,
X is a radical of the formula CO-O or $SO_2$-O,
Y is vinyl or a radical of the formula $C_2H_4$-Q, where Q is a group which is detachable under alkaline reaction conditions,
the ring A may be substituted and benzofused,
the ring B is substituted and may be benzofused, and
the ring C may be substituted, the use thereof for dyeing or printing hydroxyl- or nitrogen-containing organic substrates, and novel hydrazones.

2 Claims, No Drawings

REACTIVE FORMAZAN DYES AND HYDRAZONES

This is a division of application Ser. No. 08/117,686, filed on Sep. 8, 1993, now pending.

The present invention relates to novel formazan dyes of the formula I

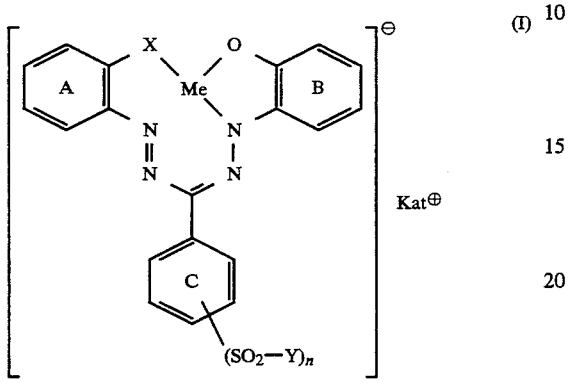

where
n is 1 or 2,
Kat• is the equivalent of a cation,
Me is copper or nickel,
X is a radical of the formula CO-O or $SO_2$-O,
Y is vinyl or a radical of the formula $C_2H_4$-Q, where Q is a group which is detachable under alkaline reaction conditions,
the ring A may be substituted and benzofused,
the ring B is substituted and may be benzofused, and the ring C may be substituted,
to the use thereof for dyeing or printing hydroxyl- or nitrogen-containing organic substrates, and to novel hydrazones.

Metal complex formazan dyes with the reactive groups are known per se; see for example EP-A-28 788. However, the prior art dyes frequently have defects in their application properties.

It is an object of the present invention to provide novel formazan-based reactive dyes which are notable for an advantageous application property profile.

We have found that this object is achieved by the formazan dyes of the formula I defined at the beginning.

Emphasis is given to formazan dyes of the formula Ia

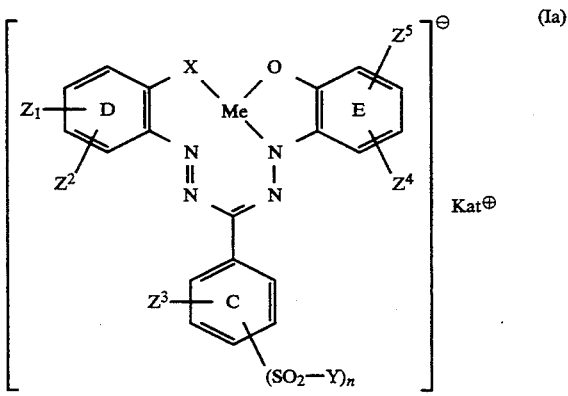

where $Z^1$ is hydrogen or hydroxysulfonyl,
$Z^2$ is hydrogen, $C_1$-$C_4$-alkanoylamino, halogen or nitro,
$Z^3$ is hydrogen, halogen, $C_1$-$C_4$-alkyl, $C_1$-$C_4$-alkoxy, $C_1$-$C_4$-alkylsulfonyl, nitro or hydroxysulfonyl,
$Z^4$ and $Z^5$ are independently of one another hydroxysulfonyl, halogen, nitro, carboxyl, ureido, substituted or unsubstituted mono- or di($C_1$-$C_4$-alkyl)ureido, substituted or unsubstituted phenylureido, substituted or unsubstituted phenyl, substituted or unsubstituted $C_1$-$C_4$-alkanoylamino, substituted or unsubstituted benzoylamino, $C_1$-$C_4$-alkoxycarbonylamino, substituted or unsubstituted mono- or dialkylcarbamoyl, substituted or unsubstituted mono- or dialkylsulfamoyl, a radical of the formula $SO_2$-Y or one of the two radicals $Z^4$ and $Z^5$ may also be hydrogen, the rings D and E may be benzofused, and n, Kat•, Me, X and Y are each as defined above.

Any alkyl appearing in the abovementioned formulae may be straight-chain or branched.

Substituted alkyl appearing in the abovementioned formula Ia may have as substituents for example hydroxysulfonyl, carboxyl, hydroxyl or sulfato. The manner of substituents is generally 1 or 2.

Any substituted phenyl appearing in the abovementioned formula Ia may have as substituents for example $C_1$-$C_4$-alkyl, $C_1$-$C_4$-alkoxy, halogen, nitro, $C_1$-$C_4$-alkanoyl, $C_1$-$C_4$-alkanoylamino, benzoylamino or hydroxysulfonyl. The number of substituents is generally from 1 to 3.

Kat• is the equivalent of a cation. It is either a proton or derived from metal or ammonium ions. Metal ions are in particular the lithium, sodium or potassium ions. Ammonium ions for the purposes of the present invention are substituted or unsubstituted ammonium cations. Substituted ammonium cations are for example monoalkyl-, dialkyl-, trialkyl-, tetraalkyl- or benzyltrialkylammonium cations or those cations which are derived from nitrogen-containing five- or six-membered saturated heterocycles, such as pyrrolidinium, piperidinium, morpholinium, piperazinium or N-alkylpiperazinium cations or their N-monoalkyl- or N,N-dialkyl-substituted products. Alkyl is used herein in the general meaning of straight-chain or branched $C_1$-$C_{20}$-alkyl which may be substituted by hydroxyl groups and/or interrupted by oxygen atoms in ether function.

Particular emphasis as cations is given to protons or lithium, sodium or potassium ions.

The radical Q is a group which is detachable under alkaline reaction conditions. Such groups are for example chlorine, bromine, $C_1$-$C_4$-alkylsulfonyl, phenylsulfonyl, $OSO_3H$, $SSO_3H$, $OP(O)(OH)_2$, $C_1$-$C_4$-alkylsulfonyloxy, substituted or unsubstituted phenylsulfonyloxy, $C_1$-$C_4$-alkanoyloxy, $C_1$-$C_4$-dialkylamino or a radical of the formula

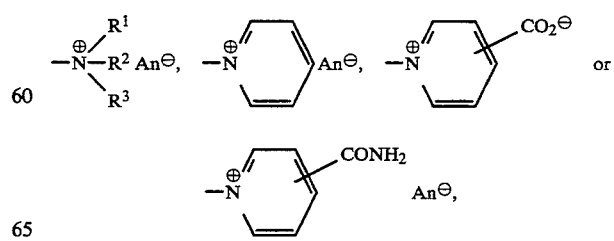

where $R^1$, $R^2$ and $R^3$ are identical or different and each is independently of the others $C_1$-$C_4$-alkyl or benzyl, and An⊖ is in each case the equivalent of an anion. Suitable anions are for example fluoride, chloride, bromide, iodide, mono-, di- or trichloroacetate, methanesulfonate, benzenesulfonate or 2- or 4-methylbenzenesulfonate.

$Z^2$, $Z^3$, $Z^4$ and $Z^5$ are each for example fluorine, chlorine or bromine.

$Z^4$ and $Z^5$ may each also be for example N-methylureido, N-ethylureido, N-propylureido, N-isopropylureido, N-butylureido, N-(2-hydroxysulfonylethyl)ureido, N-(2-sulfaroethyl)ureido, N,N-dimethylureido, N-methyl-N-(2-sulfatoethyl)ureido, phenylureido, phenyl, 2-, 3- or 4-methylphenyl, 2-, 3- or 4-methoxyphenyl, 2-, 3- or 4-chlorophenyl, 2-, 3- or 4-hydroxysulfonylphenyl, formylamino, acetylamino, propionylamino, butyrylamino, isobutyrylamino, 3-hydroxysulfonylpropionylamino, 3-carboxypropionylamino, benzoylamino, 2-, 3- or 4-hydroxysulfonylbenzoylamino, 2-, 3- or 4-chlorobenzoylamino, 2-, 3- or 4-methylbenzoylamino, 2-, 3- or 4-carboxybenzoylamino, methoxycarbonylamino, ethoxycarbonylamino, propoxycarbonylamino, isopropoxycarbonylamino, butoxycarbonylamino, carbamoyl, mono- or dimethylcarbamoyl, mono- or diethylcarbamoyl, mono- or dipropylcarbamoyl, mono- or diisopropylcarbamoyl, mono- or dibutylcarbamoyl, N-methyl-N-ethylcarbamoyl, mono-(2-hydroxysulfonylethyl)carbamoyl, sulfamoyl, mono- or dimethylsulfamoyl, mono- or diethylsulfamoyl, mono- or dipropylsulfamoyl, mono- or diisopropylsulfamoyl, mono- or dibutylsulfamoyl, N-methyl-N-ethylsulfamoyl, N-methyl-N-(2-hydroxysulfonylethyl) sulfamoyl, 2-sulfatoethylsulfonyl, 2-chloroethylsulfonyl or 2-thio sulfatoethylsulfonyl.

$Z^2$ may also be for example formylamino, acetylamino, propionylamino, butyrylamino or isobutyrylamino.

$Z^3$ may also be for example methyl, ethyl, propyl, isopropyl, butyl, isobutyl, sec-butyl, methoxy, ethoxy, propoxy, isopropoxy, butoxy, isobutoxy, sec-butoxy, methylsulfonyl, ethylsulfonyl, propylsulfonyl, isopropylsulfonyl or butylsulfonyl.

Preference is given to formazan dyes of the formula I where Me is copper.

Preference is further given to formazan dyes of the formula I where n is 1.

Preference is further given to formazan dyes of the formula I where Y is vinyl or a radical of the formula $C_2H_4$-Q, where Q is chlorine, sulfato or thiosulfato, of which particular emphasis is given to chlorine.

Particular preference is given to formazan dyes conforming to the formula Ib

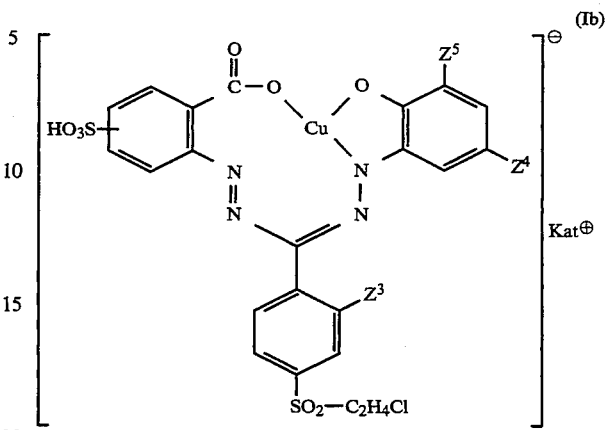

where
$Z^3$ is hydrogen or chlorine, and
$Z^4$, $Z^5$ and Kat● are each as defined above.

Emphasis is given to formazan dyes of the formula Ic

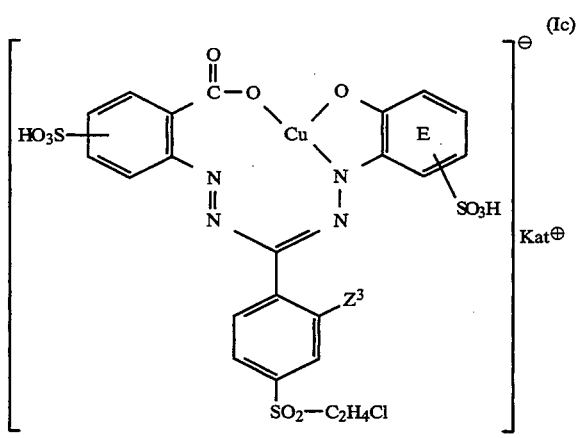

where
$Z^3$ is hydrogen or chlorine, and the ring E and Kat● are each as defined above.

Of particular interest are formazan dyes of the formula Id

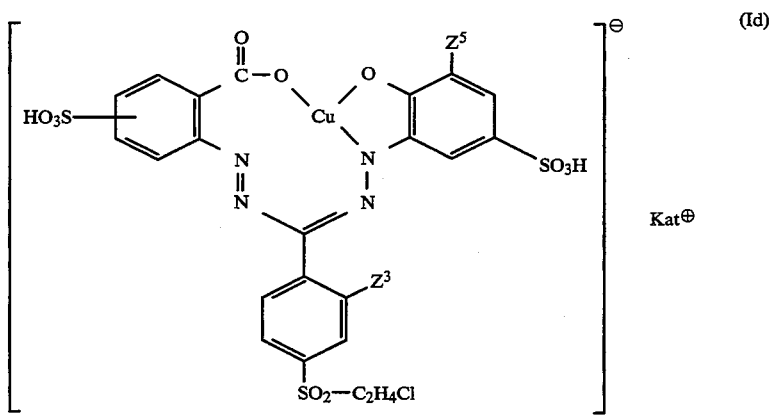

where $Z^3$ is hydrogen or chlorine, and
$Z^5$ and Kat⊕ are each as defined above.

Also of particular interest are formazan dyes of the formula Ie

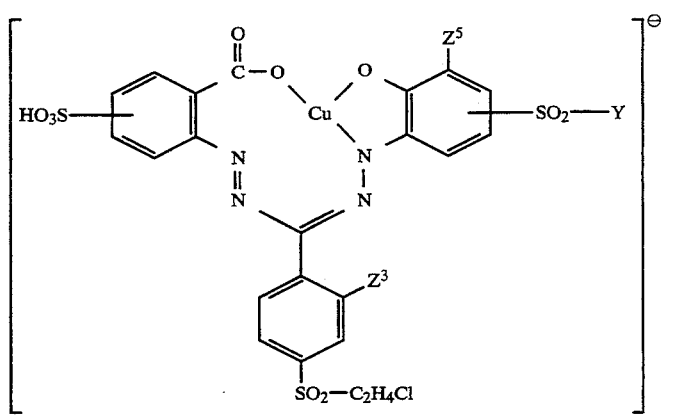

(Ie)

where
$Z^3$ is hydrogen or chlorine,
$Z^5$ is hydrogen, chlorine, bromine, nitro or hydroxysulfonyl, and
Y and Kat⊕ are each as defined above.

The novel formazan dyes of the formula I are obtainable in a conventional manner, for example by reacting a hydrazone of the formula II

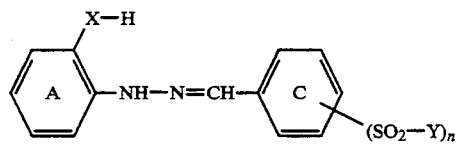

(II)

where n, X, Y and the rings A and C are each as defined above, with a diazonium salt derived from an aminophenol of the formula V

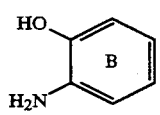

(V)

where the ring B is as defined above, in the presence of a copper or nickel salt, for example copper sulfate or nickel sulfate.

The present invention further provides hydrazones of the formula II

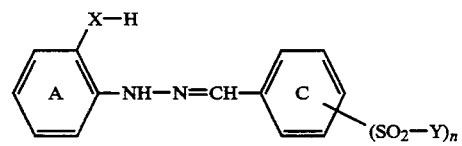

(II)

where
n is 1 or 2,
Y is vinyl or a radical of the formula $C_2H_4$-Q, where Q is a group which is detachable under alkaline reaction conditions,
X is a radical of the formula CO-O or $SO_2$-O,
the ring A may be substituted and benzofused, and the ring C may be substituted.

Preference is given to hydrazones of the formula IIa

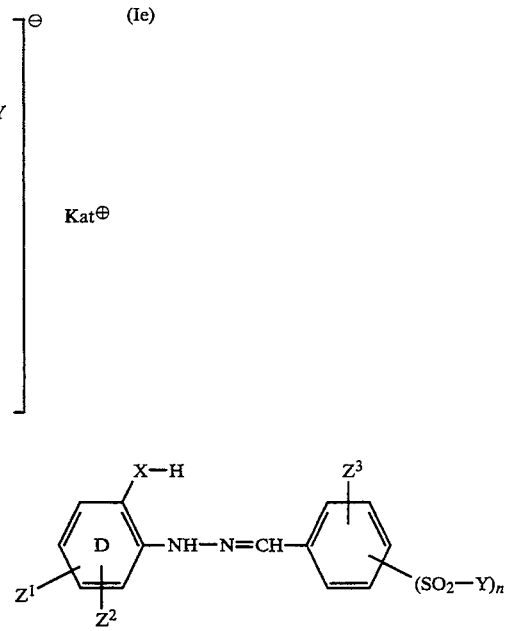

(IIa)

where
$Z^1$ is hydrogen or hydroxysulfonyl,
$Z^2$ is hydrogen, $C_1$-$C_4$-alkanoylamino, halogen or nitro,
$Z^3$ is hydrogen, halogen, $C_1$-$C_4$-alkyl, $C_1$-$C_4$-alkoxy, $C_1$-$C_4$-alkylsulfonyl, nitro or hydroxysulfonyl, the ring D may be benzofused, and n, X and Y are each as defined above.

The novel hydrazones of the formula II are obtainable with advantage by condensing for example a phenylhydrazine of the formula III

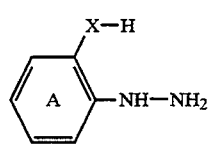

(III)

where X and the ring A are each as defined above, with a benzaldehyde of the formula IV

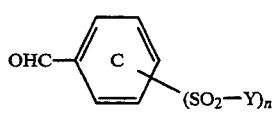

(IV)

where n, Y and the ring C are each as defined above, at from 30° to 95° C. and at pH 1–5.5 in an aqueous medium.

The pH can be set for example using hydrochloric acid or sulfuric acid.

The phenylhydrazines employed in the process of the invention are obtainable in a conventional manner, as described in Houben-Weyl, Methoden der Organischen Chemie, Volume 10/2, pages 169 ff.

The benzaldehydes of the formula IV are described in the earlier European Patent Application No. 93107419.9

The novel formazan dyes of the formula I are advantageously usable for dyeing or printing hydroxyl- or nitrogen-containing organic substrates. Substrates of this type are for example leather or fiber material containing predominantly natural or synthetic polyamides or natural or regenerated cellulose. The novel dyes are preferably useful for dyeing and printing textile materials based on wool or in particular cotton. The dyeings obtained have violet to green hues.

In particular the dyeings on cellulose-based substrates are strong in color, high in yield of fixation and possessed of a very good light and rub fastness and excellent wet fastness properties, such as wash, chlorine bleach, peroxide bleach, alkali, seawater or perspiration fastness.

Embodiments of the invention will now be more particularly described by way of example.

EXAMPLE 1

41.8 g of the hydrazone of the formula

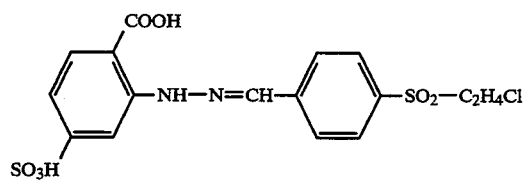

and 36.6 g of copper sulfate pentahydrate were suspended in 120 ml of water and dissolved with sodium carbonate at pH 6.5–7.0. To this solution was added, in the course of 15 to 20 minutes, the aqueous diazonium salt solution obtained by customary diazotization of 56.0 g of 2-aminophenol-4,6-disulfonic acid, while the temperature was maintained at from 10° to 20° C. and the pH with sodium carbonate at 6.0–6.5. The mixture was subsequently stirred for 1 hour until the coupling had ended (TLC). To convert the copper formazan into the stable complex form, the mixture was subsequently refluxed for 2 hours.

After cooling, the copper complex formazan compound formed was precipitated with sodium chloride, filtered off, washed with dilute aqueous sodium chloride solution and dried at 50° C. under reduced pressure to leave 103 g of the NaCl-containing dye of the formula

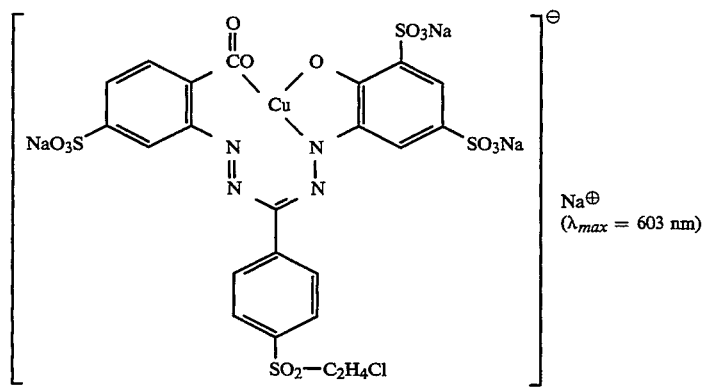

($\lambda_{max}$ = 603 nm)

EXAMPLE 2

Example 1 was repeated with 31 g of 6-acetylamino-2-aminophenol-4-sulfonic acid instead of the 56 g of 2-aminophenol-4,6-disulfonic acid, affording 93 g of the NaCl-containing dye of the formula

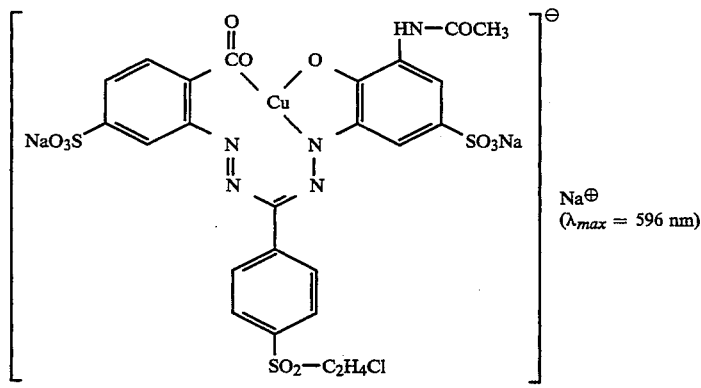

($\lambda_{max}$ = 596 nm)

EXAMPLE 3

Example 1 was repeated with the diazonium salt solution obtained by customary diazotization of 33.8 g of 6-acetylamino-2-aminophenol-4-sulfonic acid being reacted with 67.9 g of the hydrazone of the formula

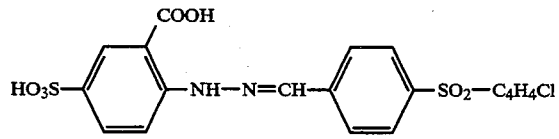

in the presence of 34.0 g of copper sulfate pentahydrate, affording 114 g of the NaCl-containing dye of the formula

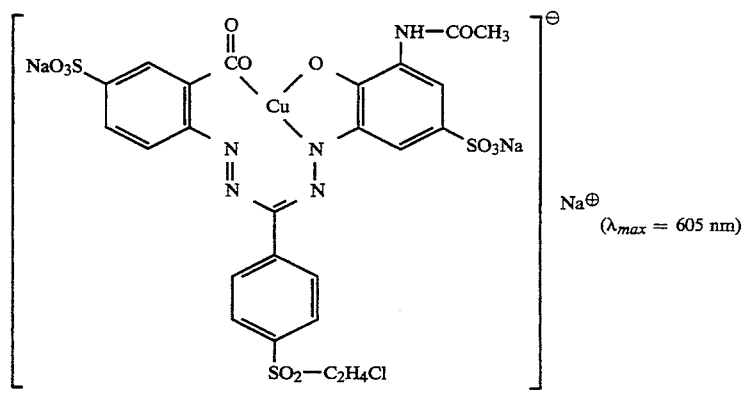

The same method gives the dyes of the formula

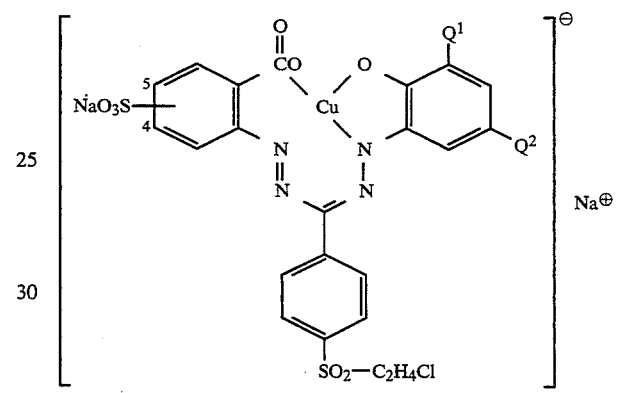

listed below in Table 1.

TABLE 1

| Ex. No. | Position of —SO₃Na | Q¹ | Q² |
|---|---|---|---|
| 4 | 4 | NH—COOC$_2$H$_5$ | SO$_3$H |
| 5 | 4 | NH—COC$_2$H$_5$ | SO$_3$H |
| 6 | 4 | NH—COC$_2$H$_4$COOH | SO$_3$H |
| 7 | 4 | H | SO$_3$H |
| 8 | 4 | Cl | SO$_3$H |
| 9 | 4 | SO$_3$H | Cl |
| 10 | 4 | NO$_2$ | SO$_3$H |
| 11 | 4 | SO$_3$H | NO$_2$ |
| 12 | 4 | NH—COCOOH | SO$_3$H |
| 13 | 4 | H | SO$_2$—N(CH$_3$)(C$_2$H$_4$SO$_3$H) |
| 14 | 4 | NH—CONH$_2$ | SO$_3$N |
| 15 | 4 | NH—COC$_2$H$_4$SO$_3$H | SO$_3$H |
| 16 | 4 | H | 4-C$_6$H$_4$—SO$_3$H |
| 17 | 4 | SO$_3$H | 4-C$_6$H$_4$—SO$_3$H |
| 18 | 4 | COOH | SO$_3$H |
| 19 | 4 | SO$_3$H | COOH |
| 20 | 4 | NH—CONHC$_2$H$_4$OSO$_3$H | SO$_3$H |
| 21 | 5 | NH—CONHC$_2$H$_4$SO$_3$H | SO$_3$H |
| 22 | 5 | NH—COC$_6$H$_5$ | SO$_3$H |
| 23 | 5 | SO$_3$H | SO$_3$H |
| 24 | 5 | NH—COOC$_2$H$_5$ | SO$_3$H |
| 25 | 5 | SO$_3$H | Cl |
| 26 | 5 | SO$_3$H | 4-C$_6$H$_4$—SO$_3$H |
| 27 | 4 | SO$_3$H | NH—COCH$_3$ |
| 28 | 4 | SO$_3$H | NH—CONH$_2$ |
| 29 | 4 | SO$_3$H | CO—NHC$_2$H$_4$SO$_3$H |

EXAMPLE 30

44.4 g of the hydrazone of the formula

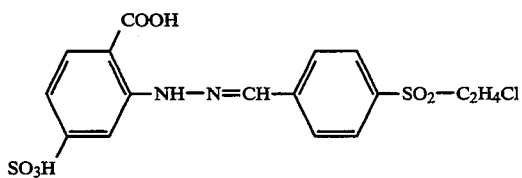

and 38.4 g of copper sulfate pentahydrate were suspended in 1 l of water at 20°-25° C. and adjusted to a pH of from 6.5 to 7.0 with 5% strength by weight aqueous sodium bicarbonate solution. Then an aqueous diazonium salt solution of 4-(2-sulfatoethylsulfonyl)-2-aminophenol, obtained by customary diazotization in aqueous solution of 29.7 g of this aminophenol, was added at from 5 to 15° C. while the pH was maintained at from 5.5 to 6.5 with sodium carbonate. The reaction mixture was subsequently stirred for 12 hours until the coupling reaction had ended. The reaction mixture pH was reduced to 1 with concentrated hydrochloric acid and the acidic solution subsequently stirred for 2 hours. Sodium bicarbonate was added to obtain a pH of from 6.0 to 6.5, and the copper complex formazan compound formed was precipitated with sodium chloride, filtered off, washed with dilute sodium chloride solution and dried at 40° C. under reduced pressure to leave 171 g of the NaCl-containing dye of the formula

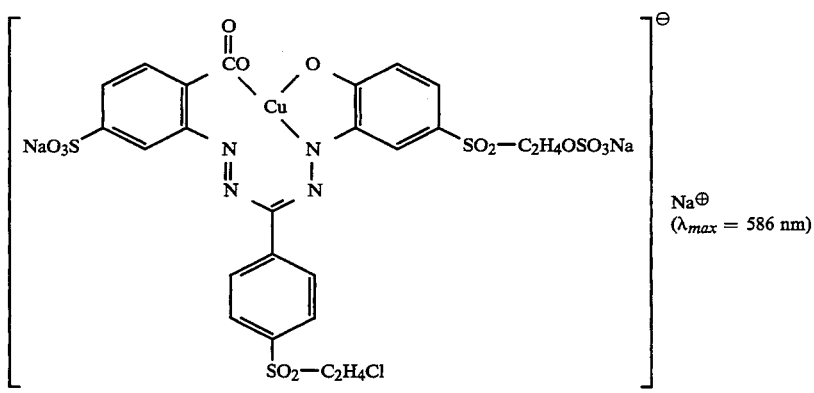

The same method gives the dyes listed below in

TABLE 2

| Ex. No. | Dye | $\lambda_{max}$ [nm] |
|---|---|---|
| 31 | | 601 |
| 32 | | 590 |

TABLE 2-continued

| Ex. No. | Dye | $\lambda_{max}$ [nm] |
| --- | --- | --- |
| 33 | (structure) | 598 |
| 34 | (structure) | 596 |

EXAMPLE 35

64.4 g of the hydrazone of the formula

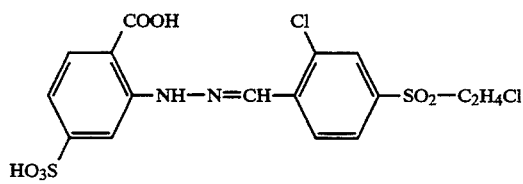

and 34.0 g of copper sulfate pentahydrate were suspended in 260 ml of water and dissolved at pH 6.5–7.0 with sodium carbonate. This solution was admixed over 15–20 minutes with the aqueous diazonium salt solution obtained by customary diazotization of 59.5 g of 2-aminophenol-4,6-disulfonic acid while the temperature was maintained at from 10° to 25° C. and the pH with sodium carbonate at from 6.0 to 6.5. The mixture was subsequently stirred for 8 hours until the coupling reaction had ended (TLC) and was then refluxed for 2 hours to convert the copper formazan into the stable complex form. After cooling, the copper complex formazan compound formed was precipitated with sodium chloride, filtered off, washed with dilute aqueous sodium chloride solution and dried at 50° C. under reduced pressure to leave 168 g of the NaCl-containing dye of the formula

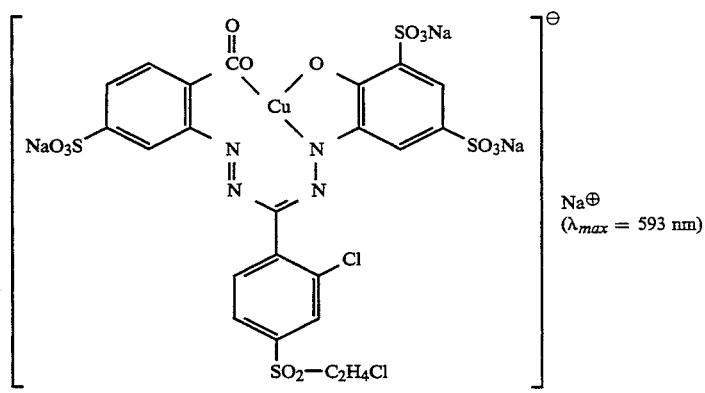

The same method gives the dyes of the formula

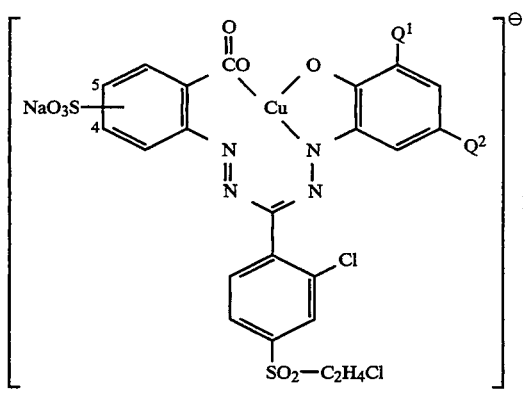

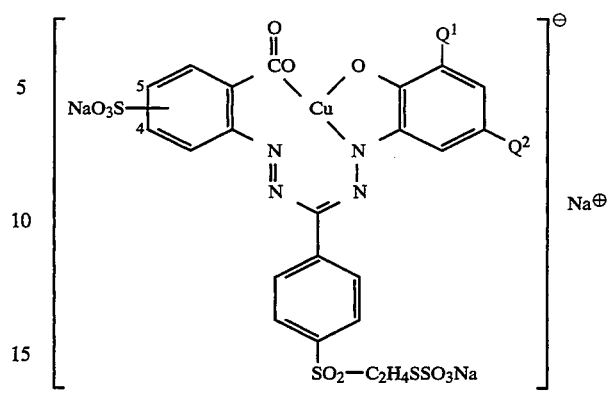

listed below in Table 3.

listed below in Table 4.

TABLE 3

| Ex. No. | Position of —SO$_3$Na | Q$^1$ | Q$^2$ |
|---|---|---|---|
| 36 | 4 | NH—COCH$_3$ | SO$_3$H |
| 37 | 4 | H | SO$_2$—C$_2$H$_4$OSO$_3$H |
| 38 | 4 | SO$_3$H | SO$_2$—C$_2$H$_4$OSO$_3$H |
| 39 | 5 | SO$_3$H | SO$_2$—C$_2$H$_4$OSO$_3$H |
| 40 | 4 | NH—COOC$_2$H$_5$ | SO$_3$H |
| 41 | 4 | NH—COC$_2$H$_5$ | SO$_3$H |
| 42 | 5 | Cl | SO$_3$H |
| 43 | 4 | COOH | SO$_3$H |

TABLE 4

| Ex. No. | Position of —SO$_3$Na | Q$^1$ | Q$^2$ |
|---|---|---|---|
| 45 | 4 | SO$_3$H | SO$_3$H |
| 46 | 4 | NH—COOC$_2$H$_5$ | SO$_3$H |
| 47 | 5 | NH—COCH$_3$ | SO$_3$H |
| 48 | 4 | H | SO$_2$—C$_2$H$_4$OSO$_3$H |
| 49 | 4 | SO$_3$H | SO$_2$—C$_2$H$_4$OSO$_3$H |
| 50 | 5 | SO$_3$H | SO$_2$—C$_2$H$_4$OSO$_3$H |
| 51 | 4 | Cl | SO$_3$H |
| 52 | 5 | SO$_3$H | Cl |
| 53 | 4 | NH—COC$_6$H$_5$ | SO$_3$H |
| 54 | 4 | NH—CONH$_2$ | SO$_3$H |
| 55 | 4 | NH—CONHC$_2$H$_4$SO$_3$H | SO$_3$H |

EXAMPLE 44

Example 2 was repeated using the hydrazone of the formula

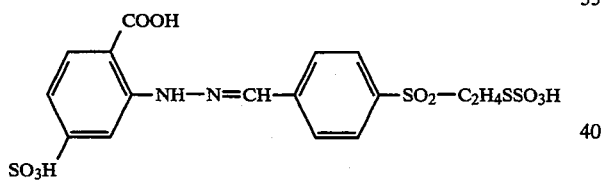

to obtain 124 g of the NaCl-containing dye of the formula

EXAMPLE 56

19.0 g of the hydrazone of the formula

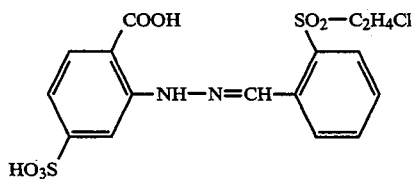

and 11.3 g of copper sulfate pentahydrate were suspended in 100 ml of water and dissolved at pH 6.5–7.0 with sodium carbonate. Then the aqueous diazonium salt solution obtained by customary aqueous diazotization of 19.7 g of 2-aminophenol-4,6-disulfonic acid was

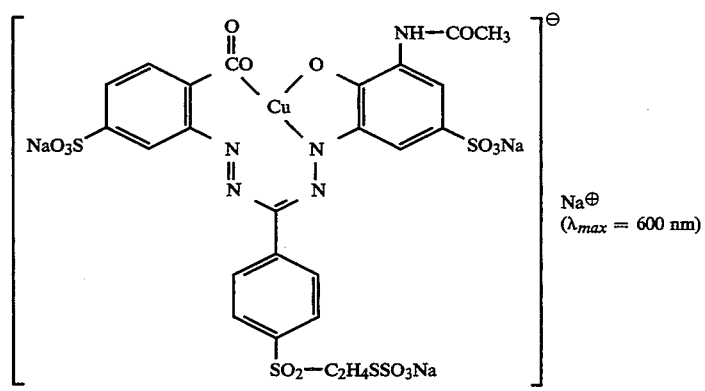

The same method gives the dyes of the formula added. The rest of the procedure was carried out as described in Example 1.

Drying left 48 g of the NaCl-containing dye of the formula

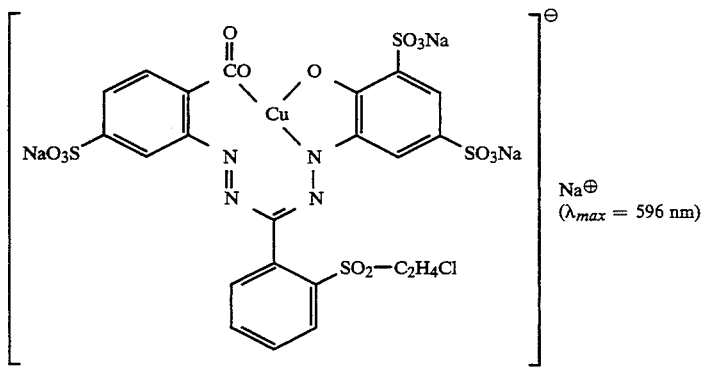

Na⊕
($\lambda_{max}$ = 596 nm)

The same method gives the dyes of the formula

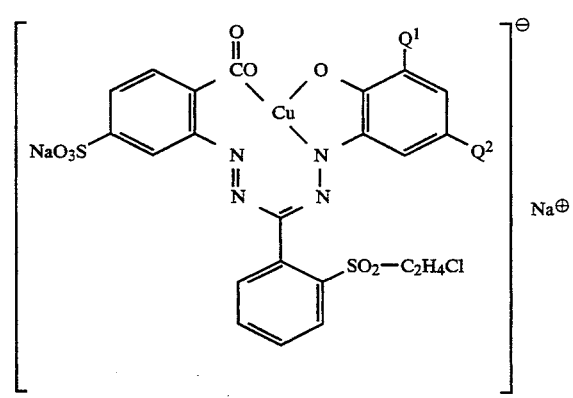

Na⊕

EXAMPLE 63

67.7 g of the hydrazone of the formula

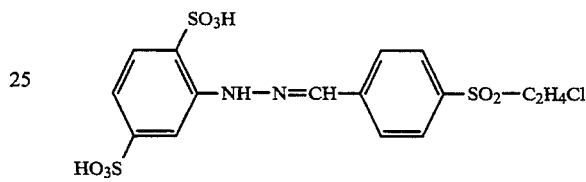

were reacted in the presence of 34 g of copper sulfate pentahydrate with an aqueous diazonium salt solution obtained by customary aqueous diazotization of 35 g of 2-aminophenol-4,6-disulfonic acid as described in Example 1.

Drying left 164 g of the NaCl-containing dye of the formula

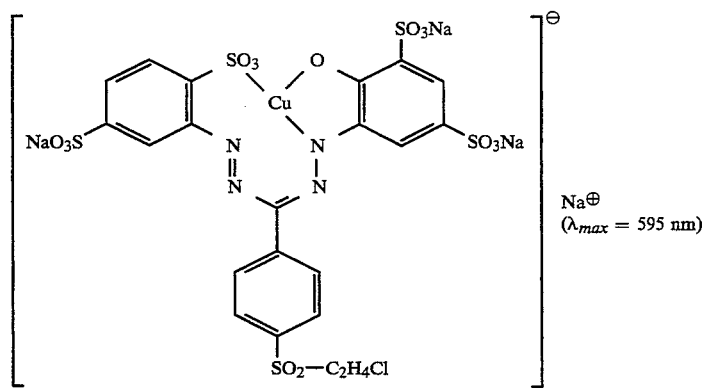

Na⊕
($\lambda_{max}$ = 595 nm)

listed below in Table 5.

TABLE 5

| Ex. No. | $Q^1$ | $Q^2$ |
|---|---|---|
| 57 | NH—COCH$_3$ | SO$_3$H |
| 58 | SO$_3$H | SO$_2$—C$_2$H$_4$OSO$_3$H |
| 59 | Cl | SO$_3$H |
| 60 | NH—COOC$_2$H$_5$ | SO$_3$H |
| 61 | NH—CONH$_2$ | SO$_3$H |
| 62 | COOH | SO$_3$H |

The same method gives the dyes of the formula

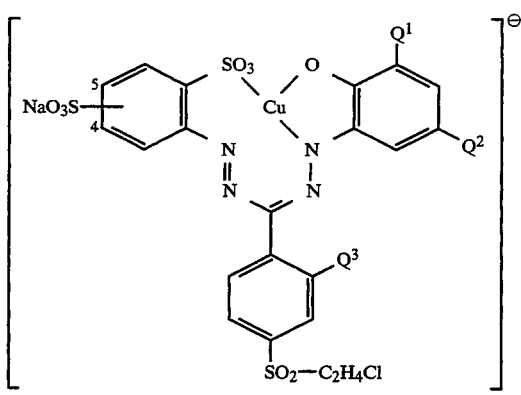

listed below in Table 6.

TABLE 6

| Ex. No. | Position of —SO$_3$Na | Q$^1$ | Q$^2$ | Q$^3$ |
|---|---|---|---|---|
| 64 | 4 | NH—COCH$_3$ | SO$_3$H | H |
| 65 | 5 | SO$_3$H | SO$_3$H | Cl |
| 66 | 5 | Cl | SO$_3$H | H |
| 67 | 3 | SO$_3$H | SO$_2$—C$_2$H$_4$OSO$_3$H | H |
| 68 | 5 | H | SO$_2$—C$_2$H$_4$OSO$_3$H | H |
| 69 | 5 | SO$_3$H | SO$_2$—C$_2$H$_4$OSO$_3$H | Cl |
| 70 | 5 | H | SO$_2$—C$_2$H$_4$OSO$_3$H | Cl |
| 71 | 5 | NH—CONH$_2$ | SO$_3$H | H |
| 72 | 4 | NH—CONHC$_2$H$_4$OSO$_3$H | SO$_3$H | Cl | ture was maintained at from 10° to 20° C. and the pH with sodium carbonate at from 6.0 to 6.5.

The mixture was subsequently stirred at room temperature for 5 hours, and then the copper complex formazan compound formed was precipitated with sodium chloride, filtered off, washed with dilute aqueous sodium chloride solution and dried at 50° C. under reduced pressure to leave 231 g of the NaCl-containing dye

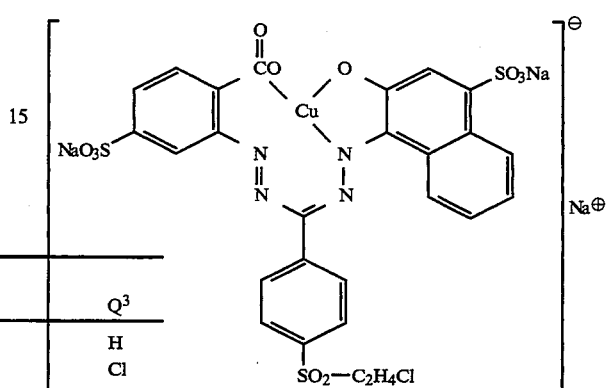

EXAMPLE 73

58.05 g of the hydrazone of the formula

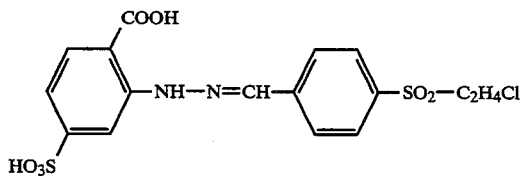

and 34.0 g of copper sulfate pentahydrate were suspended in 320 ml of water and dissolved at pH 6.5–7.0 with sodium carbonate. To this mixture was added a solution of 87.6 g of diazoxidic acid while the tempera- It dyes cotton in green shades having good wet and light fastness properties.

The same method gives the dyes listed below in Table 7. (The copper complex dyes obtained in Examples 76 to 79 were converted into the respective stabler complex form by subsequent stirring at pH 1 as described in Example 30.)

TABLE 7

| Ex. No. | Dye | Color |
|---|---|---|
| 74 | (structure shown) | green |

TABLE 7-continued
| Ex. No. | Dye | Color |
|---|---|---|
| 75 | 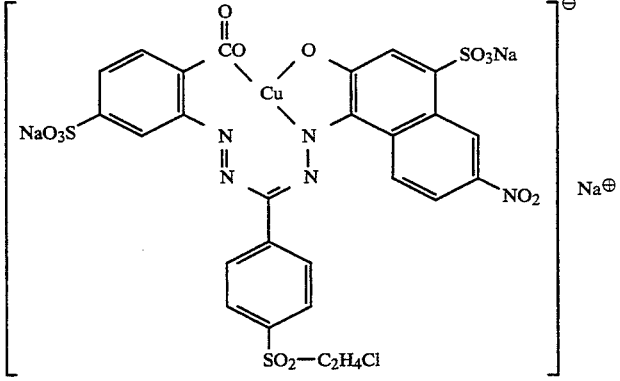 | green |
| 76 | 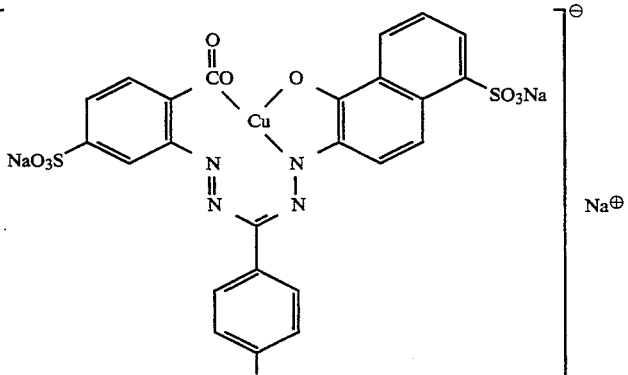 | green after after-treatment: greenish blue |
| 77 | 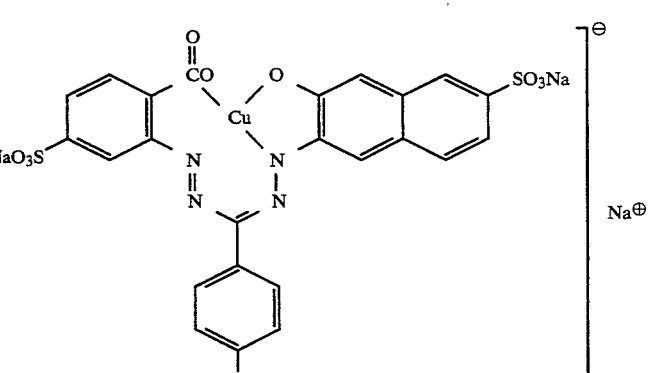 | green after after-treatment: blue |
| 78 | 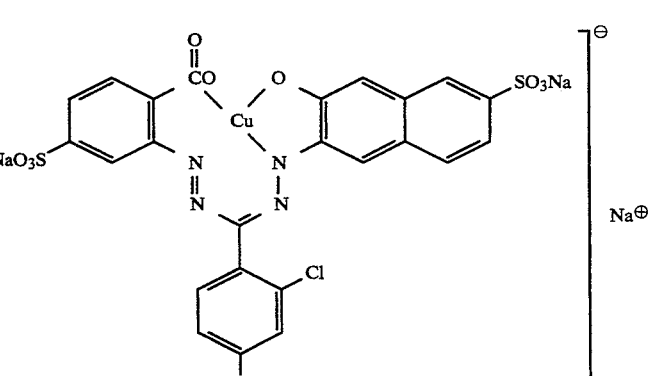 | green after after-treatment: violet |

TABLE 7-continued

| Ex. No. | Dye | Color |
|---|---|---|
| 79 | (structure shown) | green after aftertreatment: blue |

EXAMPLE 80

66.9 g of 2-carboxyphenylhydrazine-5-sulfonic acid were dissolved in 300 ml of water at pH 6 using 10% strength by weight sodium hydroxide solution. 66.9 g of 4-(2-chloroethylsulfonyl)benzaldehyde were added, and the mixture was brought to pH 1 with 7.5 ml of concentrated hydrochloric acid. It was then heated to 85°–90° C. and subsequently stirred at that temperature for about 4 hours until monitoring with TLC showed complete condensation; at the same time the pH was maintained at from 1.0 to 1.3 with 10% strength by weight hydrochloric acid. After cooling, the hydrazone formed was filtered off with suction, washed neutral with water and dried at 40° C. under reduced pressure to leave 119 g of the hydrazone of the formula

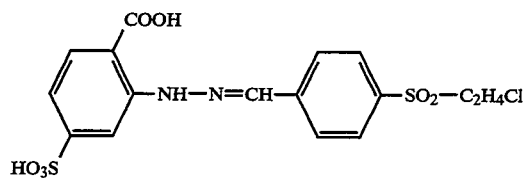

(purity>98%—HPLC) $Cl_{obs.}=7.51$ $Cl_{calc}=7.93$
$^1$H-NMR (DMSO): $\delta = 3.90$ ($CH_2CH_2$), 7.30, 7.95, 8.00, 8.20, 8.30 ( aromatic H, CH=N), 11.5 (NH) ppm
$^{13}$C-NMR (DMSO): $\delta = 36.4$, 56.9, 110.8, 111.0, 116.0, 126.7, 128.3, 131.2, 138.1, 139.0, 140.5, 146.2, 152.8, 169.0 ppm The method of Example 80 gives the hydrazones listed below in Table 8.

TABLE 8

| Ex. No. | Hydrazone |
|---|---|
| 81 | $HO_3S$—⟨⟩—NH—N=CH—⟨⟩—$SO_2$—$C_2H_4Cl$ (COOH) |
| 82 | (COOH, Cl) ⟨⟩—NH—N=CH—⟨⟩—$SO_2$—$C_2H_4Cl$, $HO_3S$ |
| 83 | (COOH, Cl) $HO_3S$—⟨⟩—NH—N=CH—⟨⟩—$SO_2$—$C_2H_4Cl$ |
| 84 | (COOH) ⟨⟩—NH—N=CH—⟨⟩—$SO_2$—$C_2H_4SSO_3H$, $HO_3S$ |
| 85 | (COOH, $SO_2$—$C_2H_4Cl$) ⟨⟩—NH—N=CH—⟨⟩, $HO_3S$ |
| 86 | (COOH, $SO_2$—$C_2H_4Cl$) ⟨⟩—NH—N=CH—⟨⟩—$SO_2$—$C_2H_4Cl$, $HO_3S$ |
| 87 | (COOH) ⟨⟩—NH—N=CH—⟨⟩—$SO_2$—$C_2H_4Cl$, $HO_3S$ |
| 88 | ($SO_3H$ naphthalene $SO_3H$)—NH—N=CH—⟨⟩—$SO_2$—$C_2H_4Cl$ |

We claim:
1. A hydrazone of the formula II

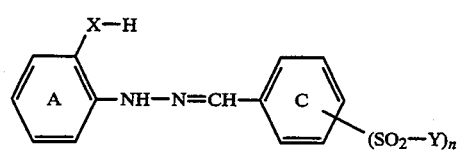

where n is 1 or 2,

Y is vinyl or a radical of the formula $C_2H_4$-Q, where Q is a group which is detachable under alkaline reaction conditions, X is a radical of the formula CO-O or $SO_2$-O, the ring A may be substituted and benzofused, and the ring C may be substituted.

2. A hydrazones as claimed in claim 1, conforming to the formula IIa

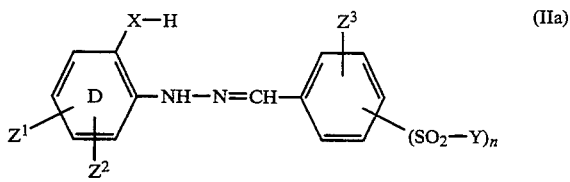

where
- $Z^1$ is hydrogen or hydroxysulfonyl,
- $Z^2$ is hydrogen, $C_1$-$C_4$-alkanoylamino, halogen or nitro,
- $Z^3$ is hydrogen, halogen, $C_1$-$C_4$-alkyl, $C_1$-$C_4$-alkoxy, $C_1$-$C_4$-alkylsulfonyl, nitro or hydroxysulfonyl, the ring D may be benzofused, and n, X and Y are each as defined in claim 1.

* * * * *